US006993381B2

(12) United States Patent
Connolly et al.

(10) Patent No.: US 6,993,381 B2
(45) Date of Patent: Jan. 31, 2006

(54) LINKING NEUROPHYSIOLOGICAL AND NEUROPSYCHOLOGICAL MEASURES FOR COGNITIVE FUNCTION ASSESSMENT IN A PATIENT

(76) Inventors: John F. Connolly, c/o Dalhousie University, Halifax, Novia Scotia (CA) B3H 4J1; Yannick Marchand, c/o Dalhousie University, Halifax, Nova Scotia (CA) B3H 4J1; Ryan C. N. D'Arcy, c/o 435 Ellice Avenue, Winnipeg, Manitoba (CA) R3B 1Y6

( * ) Notice: Subject to any disclaimer, the term of this patent is extended or adjusted under 35 U.S.C. 154(b) by 0 days.

(21) Appl. No.: 10/690,845

(22) Filed: Oct. 23, 2003

(65) Prior Publication Data

US 2004/0138582 A1    Jul. 15, 2004

Related U.S. Application Data

(60) Provisional application No. 60/421,095, filed on Oct. 25, 2002.

(51) Int. Cl.
*A61B 5/04* (2006.01)
(52) U.S. Cl. .................................... 600/544; 600/545
(58) Field of Classification Search ......... 600/544–545
See application file for complete search history.

(56) References Cited

U.S. PATENT DOCUMENTS

| | | | | |
|---|---|---|---|---|
| 4,932,416 A | * | 6/1990 | Rosenfeld | 600/544 |
| 5,243,517 A | * | 9/1993 | Schmidt et al. | 600/544 |
| 5,363,858 A | * | 11/1994 | Farwell | 600/544 |
| 6,434,419 B1 | * | 8/2002 | Gevins et al. | 600/544 |
| 6,754,524 B2 | * | 6/2004 | Johnson, Jr. | 600/544 |
| 2003/0013981 A1 | * | 1/2003 | Gevins et al. | 600/544 |

* cited by examiner

*Primary Examiner*—Max F. Hindenburg
*Assistant Examiner*—Patricia Mallari
(74) *Attorney, Agent, or Firm*—Adrian D. Battison; Michael R. Williams; Ryan W. Dupuis (57) ABSTRACT

A method for cognitive function assessment in a patient uses the ERP waveform features and parameters that maximize the correlation between the ERP components and behavioral performance on a neuropsychological test of language comprehension (PPVT-R). The method provides an electrophysiological diagnostic technique that can be used in the assessment of aphasic patients. ERPs are recorded during a computerized version of the Peabody Picture Vocabulary Test-Revised (PPVT-R, Form M). In the computerized version, a picture is presented followed by a congruent or incongruent spoken word. A derived measure is calculated from the ERP differentiation between congruent and incongruent words. The N400 is the primary component elicited to incongruent spoken words.

20 Claims, 5 Drawing Sheets

LINKING NEUROPHYSIOLOGICAL AND NEUROPSYCHOLOGICAL MEASURES FOR COGNITIVE FUNCTION ASSESSMENT IN A PATIENT

This application claims the benefit of provisional application No. 60/421,095 filed Oct. 25, 2002.

This invention relates to a method for cognitive function assessment in a patient. The invention is based upon a novel quantification technique which links ERPs with neuropsychological data at an unprecedented level. Given the high correlation, a regression line is used to estimate a patient's language ability using only ERPs.

BACKGROUND OF THE INVENTION

Event-related brain potentials (ERPs) are derived from electroencephalographic (EEG) recordings that are time-locked to a stimulus event and represent the brain's 'on-line' response during sensory and cognitive processing (Luck and Girelli, 1998). Prior work has shown that neuropsychological tests can be adapted for computer presentation and simultaneous ERP recordings (Connolly and D'Arcy, 2000; Connolly et al., 2000). One of the main applications of this approach involves the use of ERPs to assess patients with apparent language deficits secondary to brain injury. For example, the ability to evaluate accurately whether or not a patient can understand speech is critical to determining the type of therapeutic intervention that will most benefit the patient. Unfortunately, behavioral and/or communicative limitations following neurological damage can render the assessment of comprehension abilities difficult or even impossible. Therefore, the combination of an often used and widely accepted assessment method such as neuropsychological testing with the relatively new ability to record subtle cognitive activity using ERP techniques offers a major advantage in the assessment of aphasic patient populations. Left hemisphere stroke patients represent one group for which this situation occurs frequently because of deficits in both motor and language functions, thus limiting the efficacy of behavioral assessment methods (Enderby and Philipp, 1986; Enderby et al., 1987; Marquardsen, 1969; Morse and Montgomery, 1992; Pedersen et al., 1995; Wade et al., 1986). In these cases, ERPs can be used to evaluate the patient's language functions (Byrne et al., 1995; Connolly et al., 1999). Currently, the analysis and interpretation of the ERPs rests on predicted differences in the waveforms that result from well-known components (e.g., P300 and N400).

However, the analysis of the component differences in ERP waveforms would benefit greatly from a quantification procedure that allows for a direct comparison to traditional neuropsychological scores. When attempting to link quantitatively ERP and standardized neuropsychological measures there are at least two considerations that must be made. First, care must be taken to maintain the neuropsychological test properties during computer adaptation. Second, the presence or absence of the cognitive function under investigation must be determined by the existence of a predicted ERP component, which has been shown previously to reflect that function. In addition, selecting a test with graded levels of difficulty and sampling a population with varying degrees of deficits are helpful to characterize better the relationship between ERP and neuropsychological measures.

An excellent candidate that meets the criteria discussed above is the Peabody Picture Vocabulary Test—Revised (PPVT-R; Dunn and Dunn, 1981). The PPVT-R is a well-known test of vocabulary knowledge that involves matching a picture to a spoken word. Previous studies have shown that the PPVT-R can be adapted successfully for computer presentation and simultaneous ERP recording while maintaining the psychometric properties of the original test (Connolly et al., 1995). Moreover, the PMN (phonological mismatch negativity) and N400 components are elicited to the incongruent (or mismatching) spoken word stimuli in the computerized PPVT-R (Byrne et al., 1995a,b; Connolly et al., 1995). The PMN is an early negativity (~275 ms) that is associated with phonological processing in speech perception (Connolly and Phillips, 1994; Connolly et al., 2001). The N400 is a well-defined negative-going waveform (~400 ms) that is linked to semantic analysis in both speech processing and reading (Connolly and Phillips, 1994; Connolly et al., 1995; Holcomb and Neville, 1990; Kutas, 1997; Kutas and Van Petten, 1994).

The following references may be relevant to this invention:

Byrne J M, Dywan C, Connolly J F. An innovative method to assess the receptive vocabulary of children with cerebral palsy using event-related brain potentials. J Clin Exp Neuropsychol 1995;17:9–19.

Byrne J M, Dywan C, Connolly J F. Assessment of children's receptive vocabulary using brain event-related potentials: Development of a clinically valid test. Child Neuropsychol 1995;1:211–223.

Connolly J F, Phillips N A. Event-related potential components reflect phonological and semantic processing of the terminal word of spoken sentences. J Cognit Neurosci 1994;6(3):256–266.

Connolly J F, Byrne J M, Dywan C A. Assessing adult receptive vocabulary with event-related potentials: An investigation of cross-modal and cross-form priming. J Clin Exp Neuropsychol 1995;17:548–565.

Connolly J F, Mate-Kole C C, Joyce B M. Global aphasia: an innovative assessment approach. Arch Phys Med Rehabil 1999;80(10):1309–1315.

Connolly J F, D'Arcy R C N. Innovations in neuropsychological assessment using event-related brain potentials. Int J Psychophysiol 2000;37(1):31–47.

Connolly J F, D'Arcy R C N, Newman R L, Kemps R. The application of cognitive event-related brain potentials (ERPs) in language-impaired individuals: review and case studies. Int J Psychophysiol 2000;38:55–70.

Connolly J F, Service E, D'Arcy R C N, Kujala A, Alho A. Phonological aspects of word recognition as revealed by high-resolution spatio-temporal brain mapping. NeuroReport 2001; 12(2):237–243.

Dunn L M, Dunn L M. Peabody Picture Vocabulary Test-Revised. Minnesota: American Guidance Service, 1981.

Enderby P, Philipp R. Speech and language handicap: Towards knowing the size of the problem. Br J Disord Commun 1986;21(2):151–165.

Enderby P, Wood V A, Wade D T, Hewer R L. Aphasia after stroke: a detailed study of recovery in the first 3 months. Int Rehabil Med 1987;8(4):162–165.

Holcomb P J, Neville, H J. Auditory and visual semantic priming in lexical decision: a comparison using evoked potentials. Lang Cogn Proc 1990,5:281–312.

Kutas M. Views on how the electrical activity that the brain generates reflects the functions of different language structures. Psychophysiology 1997;34:383–98.

Kutas M, Van Petten C. Psycholinguistics electrified: Event-related brain potential investigations. In: Gernsbacher M A, editor. Handbook of Psycholinguistics. San Diego: Academic Press, 1994:83–143.

Luck S, Girelli M. Electrophysiological approaches to the study of selective attention in the human brain. In: Parasuraman R, editor. The attentive brain. MIT Press: Cambridge, Mass., 1998:71–94.

Marquardsen J. The natural history of acute cerebrovascular disease: a retrospective study of 769 patients. Acta Neurol Scand 1969;Suppl 38:67–68.

Morse P A, Montgomery C E. Neuropsychological evaluation of traumatic brain injury. In: White R F, editor. Clinical Syndromes in Adult Neuropsychology: The Practitioner's Handbook. Amsterdam: Elsevier, 1992:86–176.

Oldfield R C. The assessment and analysis of handedness: The Edinburgh Inventory. Neuropsychologia 1971;9:97–113.

Pedersen P M, Jørgensen H S, Nakayama G, Raaschou H O, Olsen T S. Aphasia in acute stroke: Incidence, determinants, and recovery. Ann Neurol 1995;38:659–666.

Picton T W, Lins O G, Scherg M. The recording and analysis of event-related potentials. In: Boller F, Grafman J, editors. Handbook of Neuropsychology. Amsterdam: Elsevier, 1995:429–499.

Reinvang, I. Cognitive event related potentials in neuropsychological assessment. Neuropsychology Review 1999;9: 231–248.

Wade D T, Hewer R L, David R M, Enderby P M. Aphasia after stroke: natural history and associated defects. J Neurol Neurosurg Psychiatry 1986;49(1):11–16.

SUMMARY OF THE INVENTION

According to a first aspect of the invention there is provide a method for cognitive function assessment in a patient comprising:

adapting a neuropsychological test to a computer format to present stimuli to the patient;

simultaneously with the presentation of the test, recording a patient's electroencephalographic (EEG) activity using standard research level EEG equipment using particular bandpass settings that enable recording late-occurring "cognitive" event-related potentials (ERP) from a number of locations on a subject's head;

manipulating the recorded EEG signals in order to examine each sample of recorded EEG and average together;

applying a series of analysis algorithms that relate ERP data to obtained behavioral data in an interpretable manner;

applying a series of analysis algorithms that permit interpretation of ERP within the context of the standardized test's framework even in the absence of behavioral data;

and making prognoses of patient outcome using ERP data obtained using the computer-adapted neuropsychological tests.

Preferably the above steps are conducted in such a manner as to permit the evaluation of a patient's state of mental functioning using ERP even if the patient is unable to verbally or behaviorally perform the test in the typical fashion.

Preferably the method includes using the above steps to evaluate patient progress through medical treatment using ERP data obtained using the computer-adapted neuropsychological tests.

Preferably the analysis uses the Pearson correlation coefficient to evaluate the strength of this association.

Preferably the analysis uses waveform features and parameters that maximize the correlation between the ERP components and the neuropsychological test scores.

Preferably the function assessed is that of semantic comprehension ability and wherein the analysis uses the N400.

Preferably the function assessed is that of memory ability and wherein the analysis uses the P300 and the LPC (late positive component).

Preferably the analysis uses a discrimination which is formally expressed using serial t-scores that provide a statistical method of comparing two waveforms on a point-by-points basis to establish where they differed in time.

Preferably the analysis calculates the variance for each point in the waveform necessary to achieve the t-scores using homologous points in each of the trials that went into making up the two averaged waveforms (congruent and incongruent).

Preferably a succession of sums of t-scores is obtained for each of the three levels of difficulty across the three electrode sites (Fz, Cz and Pz).

Preferably the sums are calculated in a temporal interval that is both centered to the peak latency and increased in a step-wise fashion by 40 milliseconds (semi-intervals of 20 ms on each side of the peak).

Preferably the method provides for the analysis: one baseline case in which the sum is composed of a single t-score (at the peak); and ten different semi-intervals varying by 20 ms from 20 ms to 200 ms Preferably the method includes using the first level of the computerized PPVT in conjunction with a centro-parietal montage (Cz and Pz).

Preferably, if a linear relationship links certain elements of the ERPs to PPVT-R scores, then the correlation coefficients that numerically express this relationship is used to elucidate which waveform features are critical.

Preferably by adjusting the correlational analysis to fit these optimal waveform features (i.e., optimization), the magnitude tends to one (perfect correlation).

Preferably the features that account for the highest correlation are interpretable in a neurophysiological framework (i.e., are consistent with previously identified ERP components).

According to a second aspect of the invention there is provided a method for aphasia assessment in a patient comprising:

recording a patient's electroencephalographic (EEG) activity using standard research level EEG equipment using particular bandpass settings that enable recording late-occurring "cognitive" event-related potentials (ERP) from a number of locations on a subject's head;

manipulating the recorded EEG signals in order to examine each sample of recorded EEG and average together;

presenting both visual and auditory stimuli to the subject;

simultaneously recording of the ERP so that the resulting data can be interpreted within the context of the standard neuropsychological test;

applying a series of analysis algorithms that relate ERP data to obtained behavioral data in an interpretable manner;

applying a series of analysis algorithms that permit interpretation of ERP within the context of the standardized test's framework even in the absence of behavioral data;

and making prognoses of patient outcome using ERP data obtained using the computer-adapted neuropsychological tests.

Determination of the presence and level of mental functioning in an individual is the sine qua non to many types of therapeutic intervention. It is the standard practice in medicine to ask the patient what he/she sees as the problem, its duration, its course and its severity. An inability to communicate with the patient places an insurmountable barrier to this practice and in some circumstances is the sole reason for decisions not to treat. These circumstances occur primarily with patients who have sustained serious brain injury due to trauma or disease (e.g., stroke, traumatic head injury in an automobile accident or cerebral palsy). In such circumstances the patient is unable to communicate either verbally or behaviorally; a situation that often results in the denial of treatment, referral to a long-stay facility, and ultimately a diagnosis of persistent vegetative state. Such an outcome has, until recently, been justified due to the inability to administer standard neuropsychological tests traditionally used in these circumstances. While some patients survive in these facilities for decades, it is more often the case that they begin to show the consequences of the "vegetative state" as manifested in repeated and multiple organ failure leading to death.

Over the last several years, we have developed methods to reliably and objectively assess such non-communicative patients using brain electrical recordings (i.e., a derived measure taken from standard electroencephalographic recordings and referred to as event-related potentials, ERP). Years of basic research have demonstrated that ERP waveforms reflect a variety of cognitive functions including those related to language comprehension, memory, and attention/vigilance. We have used this functional relationship between certain ERP and mental functions, and combined it with computerized versions of the traditional neuropsychological tests normally administered to brain-injured but communicative populations. We have labeled this biomedical development the Innovative Methods of Assessment Program (IMAP).

It is possible to adapt standard neuropsychological tests to computerized versions and maintain all of the tests' psychometric features ensuring that the computerized versions are measuring exactly the same mental functions as the traditional tests. Specific ERP differences are seen between correct and incorrect test performance. These ERP differences can be observed in the absence of any verbal or behavioral response on the part of the subject being tested. In experiments with patients we have replicated all of the above findings and extended the results to demonstrate that the ERP recorded during neuropsychological tests can be used to monitor progress during therapeutic interventions. An additional advantage to such brain recordings is that therapeutically positive changes are often seen in the brain before they are manifested in behavior. This fact is often of considerable benefit to the clinician as it confirms the impact of the intervention at an earlier than usual point plus it is a source of encouragement to the patient.

One particularly notable case involved a young man who had been stabbed in the head and left with no verbal or behavioral response abilities. He is quadriplegic, thoroughly non-communicative, and diagnosed as globally aphasic due to severe brain damage. On the basis of not being able to assess his mental functioning and the assumption of a total absence of mental functioning, treatment had been denied and he was to be discharged home (a decision that was acknowledged would likely result in an early death). It is demonstrated that he is able to comprehend speech and thus had retained some language abilities and their associated memory and attention functions. On the basis of our findings, he is kept in hospital and after an intensive rehabilitation regime walked out of the hospital 4.5 months later with the only remaining disability being an inability to produce speech.

The testing procedures involved in IMAP are readily learned by a technologist and do not require extensive training or education. Equally, interpretation of the results is very straightforward with differences being easily observed by even a minimally trained technician. The elaborate statistical procedures used to confirm the observed ERP differences are of the utmost importance but need not be understood at a sophisticated level by staff implementing the IMAP procedures. The statistical methods used in IMAP are essential for optimizing the relationship between ERP measures and neuropsychological results. These methods and their underlying algorithms would, at this stage, represent the main intellectual property of the IMAP procedure. Copyrights, licenses, and industrial design protection procedures would be used for other elements.

It is also important to make clear that this technology is unique in relation to anything else currently available in the marketplace or for that matter in the research world. In fact, despite the interest this research has generated in scientific circles it remains the case that no one is publishing research along these lines. The explanation for this situation rests on the fact that no credible (or striving to be credible) scientist would blatantly copy the work of another. The fairly "mechanical" nature of the test adaptation for computerized presentation coupled with simultaneous ERP recording is so strongly associated with Dalhousie's Cognitive/Clinical Neuroscience Unit that it would be impossible to build upon it in the usual scientific research manner, it would only be possible to copy it exactly. Presently, the most advanced "cognitive" evaluation available on commercially available EEG devices (e.g., those produced by Nihon Kohden provides little more than the opportunity to produce simple stimuli that will produce low level ERP phenomena that have little or nothing to do with cognition, diagnosis of mental function, or prognosis.

Finally, the techniques subsumed under the IMAP and BrainVox names have a much broader application than that being emphasized in this report. Areas of further application include the diagnosis of learning disabilities such as dyslexia and the monitoring of an affected individual during remediation. Further, we have been able to show clear and unequivocal changes in brain activity (in the direction of normalcy) as clients progress through treatment. It is of particular importance that these brain changes frequently occur prior to any observable improvement in reading but instead herald that improvement.

Another area of application centers on the monitoring of consciousness during general anaesthetic. Patient awareness during surgery has become a major area of concern within medical practice (and a major cause of litigation). Current monitoring practices are imprecise and the use of ERP methods within the IMAP/BrainVox context offers a possible solution. Finally, the ability of IMAP/BrainVox to assess and evaluate cognitive function in brain-damaged populations provides an opportunity to detect malingering in those who would claim injury-related disabilities when in fact they are unaffected. Malingering is a major issue in remuneration for injuries as well as in workers' compensation cases. The difficulty in detecting deceitful behavior on the part of clients (experienced by even skilled clinicians) is a potential target for IMAP/BrainVox as the brain's responses cannot be masked and are thus capable of revealing if a true deficit exists. Finally, this application also has potential in the Interrogation and Investigation domain (e.g., by law enforcement officials or the military) as a tool to facilitate the detection of deceptive behavior.

Data obtained when the computerized PPVT-R was given to a group of left hemisphere stroke patients and ERPs were recorded. The ERP data were integrated with behavioral data from the standardized PPVT-R. This data set met all of the requirements mentioned above: 1) the computerized and standardized PPVT-R were psychometrically comparable (Connolly et al., 1995); 2) the PMN and N400 components were linked to processing the spoken words; 3) the PPVT-R is a graded measure of vocabulary; and 4) the patient sample is characterized by varying degrees of language impairments. On the basis of preliminary analyses, we anticipated a clear linear relationship between features of the ERPs and PPVT-R scores. From a methodological viewpoint, this assumption provided a fruitful working framework because it led to two important implications. First, a quantitative observation: If a linear relationship links certain elements of the ERPs to PPVT-R scores, then the correlation coefficients that numerically express this relationship can be used to elucidate which waveform features are critical. By adjusting the correlational analysis to fit these optimal waveform features (i.e., optimization), the magnitude must tend to one (perfect correlation). Second, a qualitative observation: The features that account for the highest correlation must be interpretable in a neurophysiological framework (i.e., must be consistent with previously identified ERP components). The objective of this paper is to describe in detail the technique of this exploratory correlational analysis.

DETAILED DESCRIPTION

The method described herein includes the following steps:

adapting a neuropsychological test to a computer format to present stimuli to the patient;

simultaneously with the presentation of the test, recording a patient's electroencephalographic (EEG) activity using standard research level EEG equipment using particular bandpass settings that enable recording late-occurring "cognitive" event-related potentials (ERP) from a number of locations on a subject's head;

manipulating the recorded EEG signals in order to examine each sample of recorded EEG and average together;

applying a series of analysis algorithms that relate ERP data to obtained behavioral data in an interpretable manner;

applying a series of analysis algorithms that permit interpretation of ERP within the context of the standardized test's framework even in the absence of behavioral data;

and making prognoses of patient outcome using ERP data obtained using the computer-adapted neuropsychological tests.

The above steps are conducted in such a manner as to permit the evaluation of a patient's state of mental functioning using ERP even if the patient is unable to verbally or behaviorally perform the test in the typical fashion.

The method uses the above steps to evaluate patient progress through medical treatment using ERP data obtained using the computer-adapted neuropsychological tests.

The analysis uses the Pearson correlation coefficient to evaluate the strength of this association.

The analysis uses waveform features and parameters that maximize the correlation between the ERP components and the neuropsychological test scores.

The function assessed is that of semantic comprehension ability and wherein the analysis uses the N400.

The function assessed is that of memory ability and wherein the analysis uses the P300 and the LPC (late positive component).

The analysis uses a discrimination which is formally expressed using serial t-scores that provide a statistical method of comparing two waveforms on a point-by-points basis to establish where they differed in time.

The analysis calculates the variance for each point in the waveform necessary to achieve the t-scores using homologous points in each of the trials that went into making up the two averaged waveforms (congruent and incongruent).

A succession of sums of t-scores is obtained for each of the three levels of difficulty across the three electrode sites (Fz, Cz and Pz).

The sums are calculated in a temporal interval that is both centered to the peak latency and increased in a step-wise fashion by 40 milliseconds (semi-intervals of 20 ms on each side of the peak).

The method provides for the analysis: one baseline case in which the sum is composed of a single t-score (at the peak); and ten different semi-intervals varying by 20 ms from 20 ms to 200 ms The method uses the first level of the computerized PPVT in conjunction with a centro-parietal montage (Cz and Pz).

If a linear relationship links certain elements of the ERPs to PPVT-R scores, then the correlation coefficients that numerically express this relationship is used to elucidate which waveform features are critical.

By adjusting the correlational analysis to fit these optimal waveform features (i.e., optimization), the magnitude tends to one (perfect correlation).

The features that account for the highest correlation are interpretable in a neurophysiological framework (i.e., are consistent with previously identified ERP components).

Patients

Ten patients (8 males and 2 females) volunteered for a study on language assessment techniques following stroke. The patients were included in the study on a consecutive admissions basis (testing occurred from Jun. 8, 2000 to Jan. 25, 2001). They were admitted to hospital following the diagnosis of a left-sided stroke and had undergone diagnostic imaging (CT and/or MRI scans) in order to identify infarct locations (see Table 1). They were all undergoing rehabilitation programs at the time of testing. Their mean age is 61.8 (SD=13.2, range=45 to 81) years and their mean education is 11.1 (SD=2.5, range=5 to 14) years. The mean number of weeks between the stroke and first day of testing is 7.6 (SD=3.9, range 3.9 to 14.6). All patients were native English-speakers and were dextral as assessed by the Edinburgh Handedness Inventory (Oldfield, 1971; Laterality Quotient (LQ) range 66.7 to 100).

Stimuli

A computerized version of Form M of the PPVT-R is used to assess receptive auditory comprehension of picture names (Byrne et al., 1995a,b; Connolly et al., 1995). This computerized PPVT-R is divided into three levels of difficulty: Level 1 (25 items) contained words from a preschooler level (2.5 to 5 years); Level 2 (40 items) contained words from a child/adolescent level (10 to 17 years); and Level 3 (25 items) contained words from an adult level (advanced vocabulary).

A single trial consisted of the presentation of a picture (e.g., picture of ball) for 1700 ms followed by a digitized spoken word (700 ms after the picture onset). The spoken words were either congruent or incongruent (e.g., 'ball' or 'car') in relation to the picture (0.5 probability). The monochromatic pictures (N=90) were adapted directly from the PPVT-R and paired with congruent and incongruent spoken words (N=180). The digitized spoken words were presented binaurally on headphones (90 dB, male voice, 20 KHz digitization rate) and their duration ranged from 750 ms to 1000 ms. A stimulus trigger is positioned manually at the beginning of the digitized waveforms for each word. The inter-trial interval is 5.2 s, during which a cross is displayed as a central fixation point.

General Procedure

Patients participated in two separate one and a half-hour testing sessions (ERP and neuropsychological), both of which always occurred within a three-day testing period (counterbalanced). It should be noted that it is not possible to administer both versions (i.e., the computerized and the traditional) of the test simultaneously. First, these patients had limited function and adding a response component to the experiment would have been an unreasonable challenge for some of them. Also, it is essential to compare the present computerized version that includes simultaneous ERP recordings with the "true" standard administration of the traditional PPVT-R. This could only be accomplished by administering the traditional test in the traditional manner, not a computerized version requiring a button press.

ERP testing occurred in a quiet room and the stimuli were presented on a computer monitor that is positioned between 75 and 100 cm away (adjusted to ensure visual acuity). Short breaks were given between each vocabulary level experiment to reduce fatigue.

Neuropsychological assessment is conducted and included the PPVT-R Form L (Dunn and Dunn, 1981) to assess auditory comprehension of picture names. The total time required to administer PPVT-R Form L is approximately 40 minutes.

Electrophysiological Recording

ERPs were recorded to the onset of the congruent and incongruent spoken words.

An electroencephalogram (EEG) is recorded from three midline sites (Fz, Cz, and Pz) and all electrodes were referenced to linked earlobes. An electro-oculogram (EOG) with electrodes placed above and on the outer canthus of the left eye is used to record ocular artifact activity. All electrodes were Ag/AgCl and impedance is kept at or below 5 KΩ. The continuous EEG data were filtered on-line with a bandpass of 0.05 Hz to 30 Hz, and digitally sampled at 1000 Hz. In the off-line analysis, the bandpass is set to 0.1 Hz to 20 Hz, with epochs beginning 100 ms prior to the stimulus onset and extending 1000 ms after the stimulus onset. All data were baseline corrected using the pre-stimulus interval and any trials with EOG artifacts ±75 $\mu$V between −100 ms and 750 ms were rejected from the analysis.

For one patient, the EOG artifact reject is subsequently adjusted to ±50 $\mu$V because oculomotor difficulties reduced the magnitude of the artifacts. For another patient, EOG channels were not reliably detecting artifact, therefore the rejection procedure also included the Fz site. The mean percentage of trials accepted in the analysis is 78.5 (SD=15.9). The EEG data were then averaged on the basis of experimental condition (i.e., Congruent and Incongruent) for all three levels of difficulty in the computerized PPVT-R.

Analysis Technique for Linking ERPs and Behavioral Performances

Correlation Coefficients

Because a strong linear relationship between the ERP features and neuropsychological data is hypothesized, the Pearson correlation coefficient (hereafter Pearson r) is used to evaluate the strength of this association. This statistic assumes a linear relationship and should be confirmed by inspection of the scatter plot. It should be noted that analyses using Spearman's rho were also conducted but provided the same results and therefore will not be discussed further.

T-Score as a Building Block of the Analysis

The PMN and N400 are the primary components elicited in the original reports (Byrne et al., 1995a,b; Connolly et al., 1995) describing ERP findings during performance of the PPVT-R. In the present study, the N400 proved to be the largest component that gave rise to the expected waveform differentiation; thus, the analysis is confined to this response. The presence of this component following a spoken word that incorrectly describes an accompanying picture reflects intact comprehension of the word meaning (Byrne et al., 1995a,b; Connolly et al., 1995). This effect occurs only if the word is within the individual's vocabulary knowledge level. If the participants are tested at vocabulary levels outside their knowledge, then the two types of averaged waveforms (congruent versus incongruent spoken words) fail to differentiate.

Therefore, the N400 differentiation between the waveforms is used as an index of comprehension. This discrimination is formally expressed using serial t-scores that provided a statistical method of comparing two waveforms on a point-by-points basis to establish where they differed in time. The variance for each point in the waveform necessary to achieve the t-scores is calculated using homologous points in each of the trials that went into making up the two averaged waveforms (congruent and incongruent). The manner in which the t-scores are used in this procedure is provided in more detail below.

Baseline and Temporal Intervals

Figure 1:
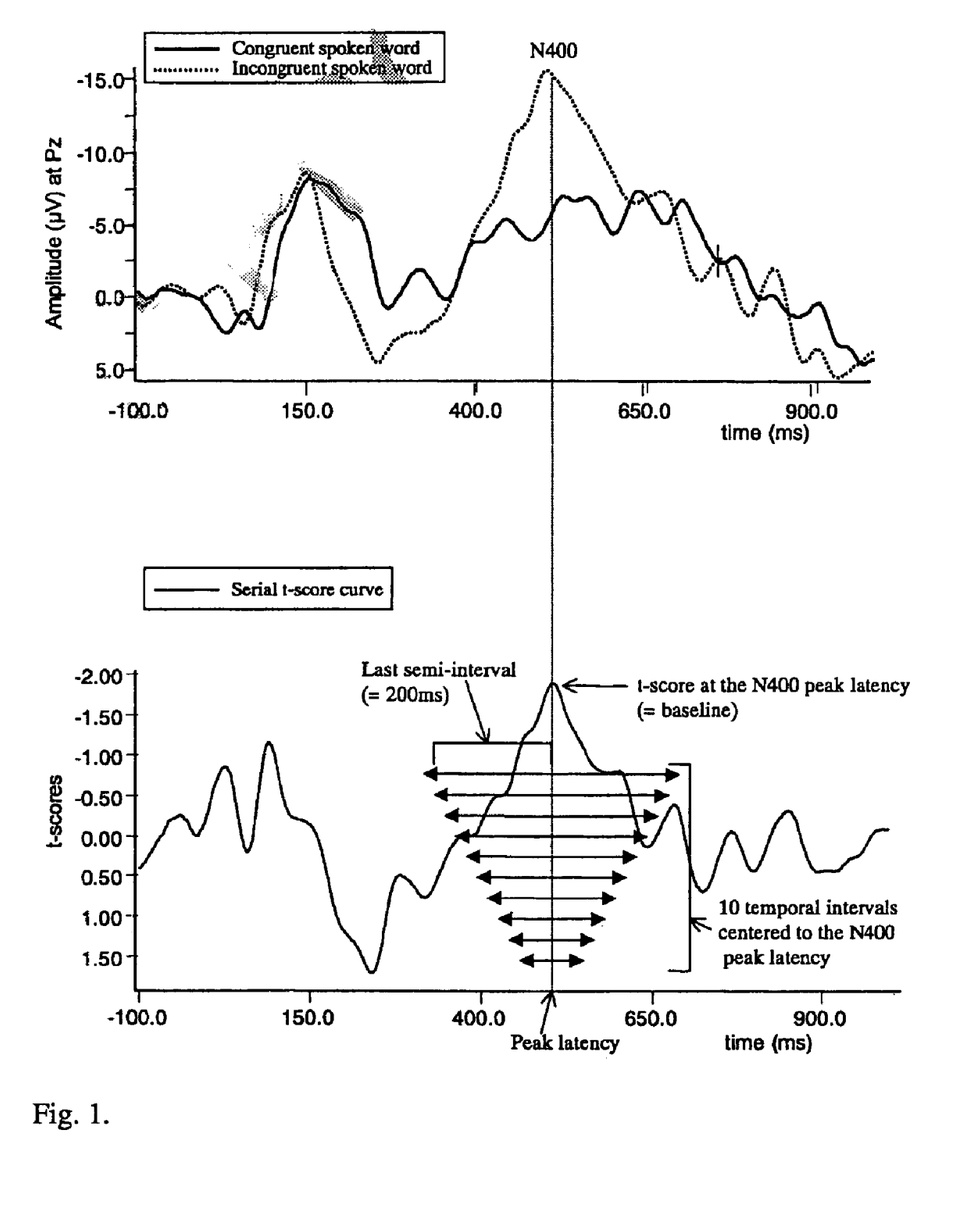
FIG. 1 is a graph in which waveforms are presented for one of the least able, most debilitated patients (LC) who obtained the second lowest score on the PPVT-R and is characterized by brain damage that included the posterior aspects of the frontal lobe, middle cerebral artery, and insular cortex. The purpose in presenting one of the most problematic patients is to demonstrate further the robust nature of the analysis routines presented in this study. The baseline and temporal intervals are defined from both of Congruent and Incongruent averaged waveforms and their corresponding serial t-scores. For the waveforms, time (ms) is on the x-axis and amplitude ($\mu$V) is on the y-axis. Negative is plotted up.

The nomenclature for ERPs is usually based on labeling different peaks in the waveforms on the basis of their polarity and latency (Picton et al., 1995). Using automatic procedures, we score the maximum negative-going peak in the incongruent condition (350 ms to 650 ms period) as the N400 (all peaks were verified visually). A succession of sums of t-scores is obtained for each of the three levels of difficulty across the three electrode sites (Fz, Cz and Pz). These sums were calculated in a temporal interval that is both centered to the peak latency and increased in a stepwise fashion by 40 milliseconds (semi-intervals of 20 ms on each side of the peak). This method provides for the analysis: one baseline case in which the sum is composed of a single t-score (at the peak); and ten different semi-intervals varying by 20 ms from 20 ms to 200 ms as shown in FIG. 1.

To furnish grounds for the further exploration of the correlational analysis and to sum up the procedure, we use the following notation where the symbol θ represents the predicted differentiation in the ERP waveforms:

θ(l,s,si) with l∈{1: Level 1, 2: Level 2, 3: Level 3}, s∈{Fz, Cz,Pz} and si∈{20 ms×i with i∈[0. . . 10]}.

θ(l,s,si) expresses for a given individual the sum of t-scores between the two averaged waveforms for the Level l of the computerized test at the site s. The quantity θ is calculated in the temporal interval [Peak−si,Peak+si], with "Peak" representing the peak latency of the component for the Level l at the site s. Thus, for example, if we have a N400 peak latency of 350 at Level 1, for the site Cz, and calculate 60 ms semi-intervals, then θ(1,Cz,60) is the value that corresponds to the sum of the serial t-scores. The temporal window therefore comprises 290 ms (350−60) to 410 ms (350+60). A few remarks need to be given about this definition:

1. The baseline is defined when i=0. In this particular case, θ(l,s,0) corresponds to a single t-score, namely, the t-score given at the N400 peak latency. This baseline is operationally defined as the t-scores used to derive the correlation coefficient without using optimization procedures.

2. In the remainder of the paper, the word semi-interval will refer to the variable si. It is worthwhile to note that the first ([peak latency−si] to peak latency) and second (peak latency to [peak latency+si]) semi-intervals can embody the onset and offset phases of the component, respectively.

3. As the analog-to-digital (A/D) conversion rate is 1000 Hz (see Method section), one t-score per millisecond is computed to form the serial t-score curve. Therefore, the number of t-scores that are summed to determine θ is equal to (2×si+1).

4. The t-score is computed such that it is algebraically negative when the expected N400 component is elicited.

5. Prior work (Byrne et al., 1995a,b; Connolly et al., 1995) has shown that it is possible to obtain a N400 in the congruent condition when the item difficulty exceeds an individual's vocabulary level. Accordingly, any t-score sums (θ value) in which the sign is positive are converted to zero.

Strategies

Once the baseline, temporal intervals, and θ have been defined, it is necessary to explain how these notions operated with the recording montage (Fz, Cz, and Pz) and the levels of difficulty (Levels 1, 2, and 3). Using semi-intervals (20 ms stepwise gradations) from 20 to 200 ms, the following twelve expressions were calculated 10 times (once for each semi-interval) plus the N400 peak, which served as baseline:

1. $S1 = \sum_{s} \theta(1, s, si)$ with $s \in \{Fz, Cz, Pz\}$;

2. $S12 = \sum_{l} \sum_{s} \theta(l, s, si)$ with $l \in \{1, 2\}, s \in \{Fz, Cz, Pz\}$;

3. $S123 = \sum_{l} \sum_{s} \theta(l, s, si)$ with $l \in \{1, 2, 3\}, s \in \{Fz, Cz, Pz\}$;

4. $S1(CzPz) = \sum_{s} \theta(1, s, si)$ with $s \in \{Cz, Pz\}$;

5. $S12(CzPz) = \sum_{l} \sum_{s} \theta(l, s, si)$ with $l \in \{1, 2\}, s \in \{Cz, Pz\}$;

6. $S123(CzPz) = \sum_{l} \sum_{s} \theta(l, s, si)$ with $l \in \{1, 2, 3\}, s \in \{Cz, Pz\}$;

7. M1=Max(θ(1,Fz,si), θ(1,Cz,si), θ(1,Pz,si));

8. $M12 = \sum_{l} \text{Max}(\theta(l, Fz, si), \theta(l, Cz, si), \theta(l, Pz, si))$ with $l \in \{1, 2\}$;

9. $M123 = \sum_{l} \text{Max}(\theta(l, Fz, si), \theta(l, Cz, si), \theta(l, Pz, si))$ with $l \in \{1, 2, 3\}$;

10. M1(CzPz)=Max(θ(1,Cz,si), θ(1,Pz,si));

11. $M12(CzPz) = \sum_{l} \text{Max}(\theta(l, Cz, si), \theta(l, Pz, si))$ with $l \in \{1, 2\}$;

12. $M123(CzPz) = \sum_{l} \text{Max}(\theta(l, Cz, si), \theta(l, Pz, si))$ with $l \in \{1, 2, 3\}$.

These equations are easily interpretable when the three main ideas that underlie them are specified. First, when visually examining the waveforms, two practical strategies can be employed to draw conclusions from the presence or absence of a given component. On the one hand, its manifestation at a single electrode site can be seen as a necessary and sufficient condition to infer that the associated cognitive function(s) occurred. On the other hand, one may give more strength and confidence to this statement if more than one occurrence is detected across the recording montage. Whereas the first part of the above equations (1 to 6) represents the additive model ("several occurrences" or SUM strategy), the second part (7 to 12) expresses the alternative option ("a single occurrence" or MAX strategy). Second, another dichotomy exists as a result of the recording montage—one based on peak topography. Because the N400 component is typically characterized by a centro-parietal topography (Kutas and Van Petten, 1994), these specific locations (Cz and Pz) can be chosen (equations 4, 5, 6, 10, 11 and 12) to be compared with the full montage (equations 1, 2, 3, 7, 8 and 9). Third, it can also be expected that a combination of successive levels of difficulty will also optimize the correlational analysis. In contrast to the first level (represented by equations 1, 4, 7 and 10), a combination of the first two levels (Levels 1 and 2) corresponds to equations 2, 5, 8 and 11 and the combination of all three levels corresponds to equations 3, 6, 9 and 12. The results for all of these 12 equations (six equations for the SUM strategy and six equations for the MAX strategy) provided an index of N400 differentiation and were subsequently correlated with behavioral performance (PPVT-R standard scores). These results were then evaluated in order to determine which one(s) produced optimal correlation coefficients (i.e., values that tend to one, see Introduction section). The results for SUM and MAX strategies were very similar with a slight advantage for the latter. As a consequence only findings based on the MAX strategy are presented.

Results

MAX Strategy

Figure 2:
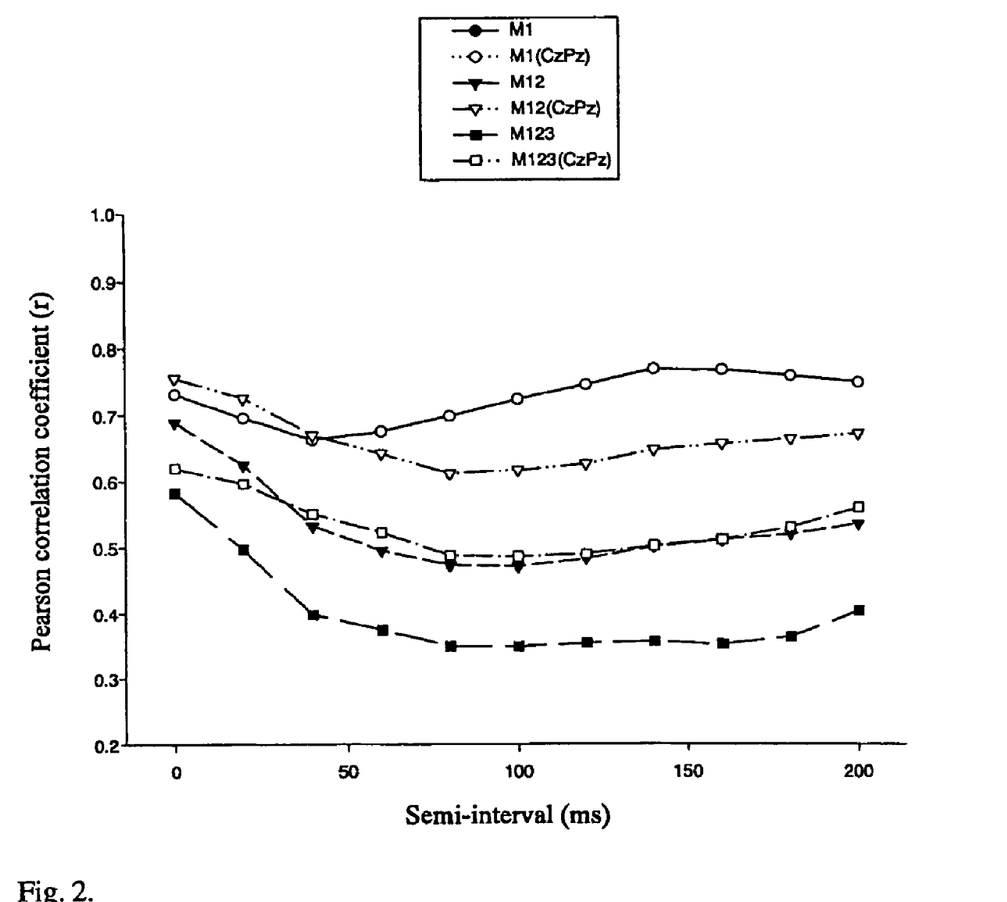
FIG. 2 is a graph showing the result of the Max strategy on Pearson correlations when applied to a set of semi-intervals. Semi-intervals (ms) are on the x-axis and coefficient values are on the y-axis. Note that M1 and M1(CzPz) overlap totally.

FIG. 2 depicts the 'correlation curves' for the MAX strategy for the Pearson r. Several critical findings were evident in these curves. First, examination of the correlation coefficients for the three levels of difficulty revealed a graded reduction from M1, M12 and M123. This result reflected the fact that the standard scores of the PPVT correlated better with N400 differentiation at Level 1 and gradually diminished as the level of difficulty increased. Second, the correlation coefficients for equations involving only the Cz and Pz sites were characteristically higher than the corresponding values from the full montage. This outcome echoed the common finding that the N400 component is typically distributed in centro-parietal regions. The best correlations were obtained within the three semi-intervals, namely, 140 ms, 160 ms and 180 ms.

Following these preliminary findings, a scaling factor is applied to the results of these three best semi-intervals obtained using the most successful equation (M1(CzPz), i.e., Equation 10) to adjust for noise in averages with an insufficient number of trials (i.e., low signal noise ratio). This optimization procedure is directed towards patient application where insufficient trial numbers (and the associated noisy data) is a fact of life. The procedure is weighted against false positives. Using the three semi-intervals identified above, the coefficients in the equation 10 (M1(CzPz)) were adjusted. The scaling process is described below.

For individual averages in which there were fewer than N trials (varying from 20–50) included in the signal averaging process, the results given by M1(CzPz) were weighted by multiplying them by [accepted trials/N-trial cut-off]. N-trial cut-offs were varied by 5 from 20 to 50 (e.g. the total number of trials at Level 1 of the computerized PPVT). The purpose of this process is to find the scaling factor that optimized the Pearson r. By iteratively combining levels of the computerized PPVT, sites, strategies and N-trial cut-off, optimal statistical correlations were found. The highest Pearson r value is 0.766 with the semi-interval of 140 ms. The best combination is obtained using the semi-interval of 160 ms and a cut-off of 40 that resulted in a Pearson r of 0.809. Their magnitude confirmed our original quantitative prediction. The correlation that links the ERPs to the PPVT-R scores can characterize the critical waveform features and, when optimized using these features, tends to one (perfect correlation).

Component Interval

Figure 3:
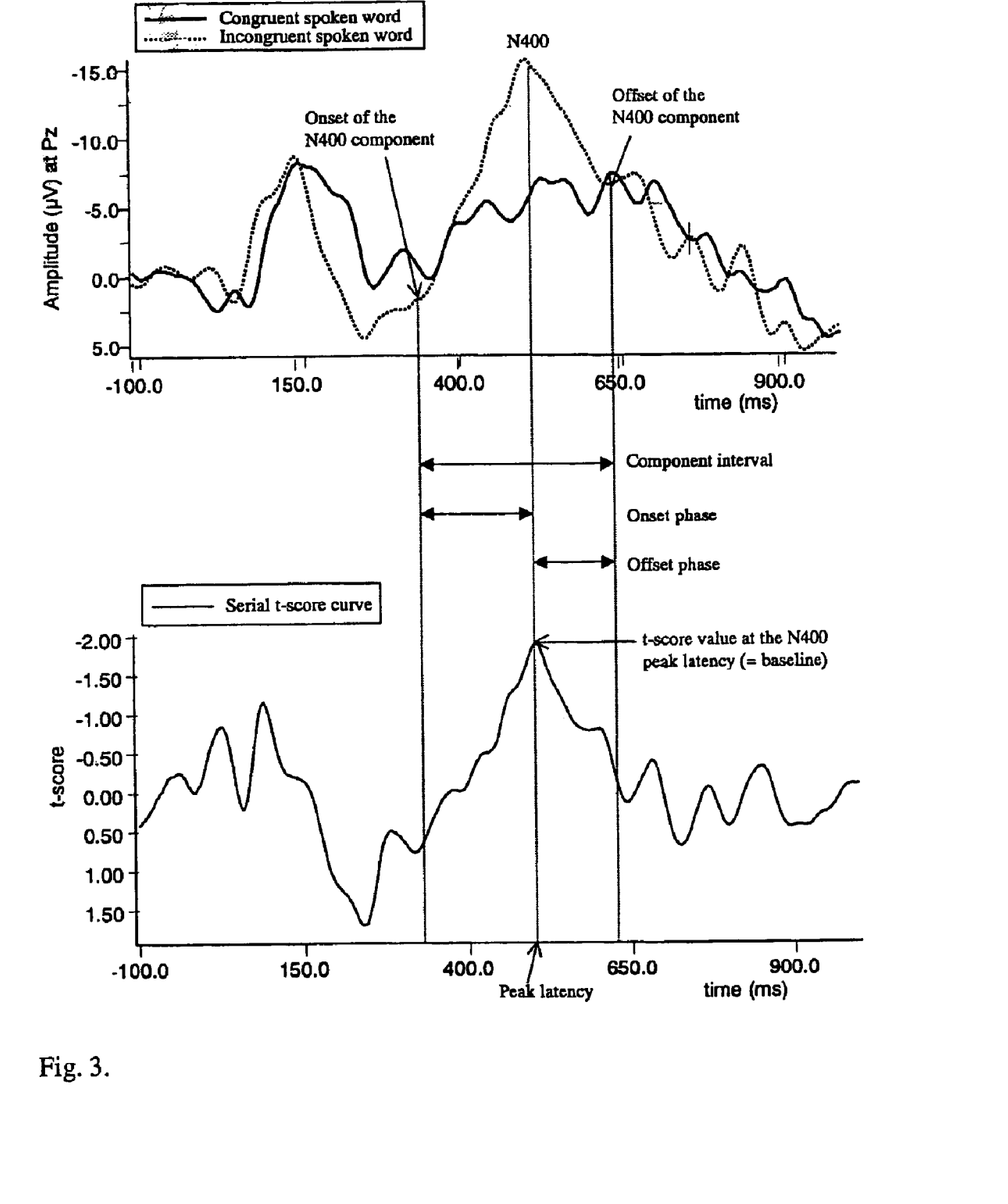
FIG. 3 is a graph showing the definition of the component interval with its onset and offset phases.

In light of the previous analysis, it is necessary to find a neurophysiological/morphological interpretation that corresponds to the semi-intervals that give the best statistical correlations between ERPs and PPVT-R scores. It is assumed that these temporal windows encapsulated the entire period in which the ERP component(s) (the N400) is (are) present. To evaluate this supposition, in addition to the initial 90 peak values (10 patient waveforms×3 levels (i.e., PPVT-R vocabulary levels)×3 sites (Fz, Cz, Pz), 20 more latency values (10 patient waveforms×1 level (i.e., PPVT-R, Level 1)×2 sites (Cz, Pz)) were scored visually. The onset and offset points (see Baseline and temporal intervals, remark # 2 hereinbefore) of the N400 component were input into the optimal equations (equations 4 and 10). Three points instead of only one now defined the N400 component and were thus segmented into three temporal intervals. FIG. 3 shows the component interval and its two subparts: the onset and offset phases. In the primary correlational analysis (above), with the different semi-intervals, isometric intervals centered at the N400 peak latency were assumed. In contrast, the component intervals did not comprise the same period of time in the onset and offset phases and varied between patients. Accordingly, the $\theta$ values to be compared in the analysis were computed on the basis of the mean (not the sum) of t-scores.

Figure 4:
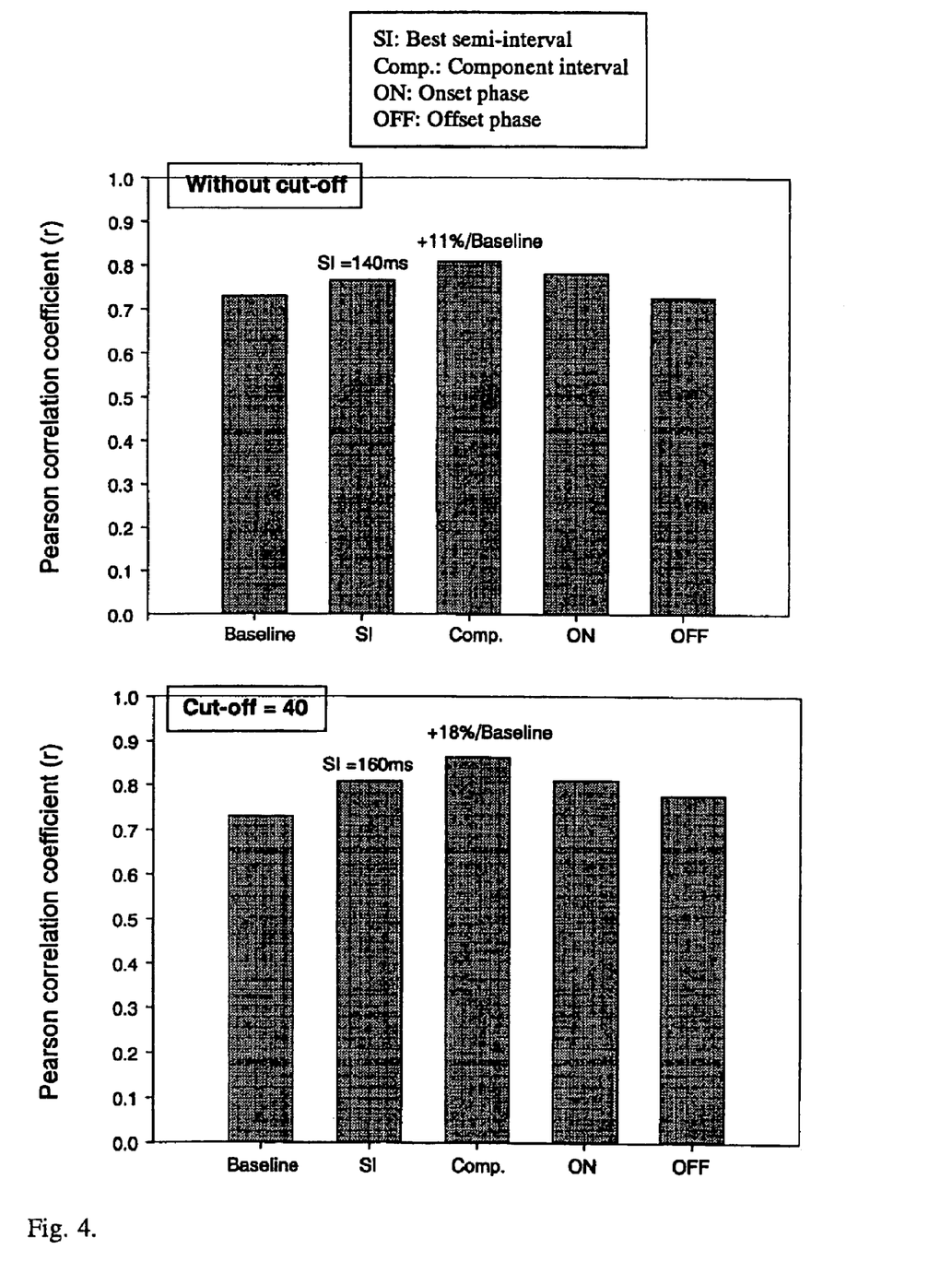
FIG. 4 is a bar chart showing comparisons between baselines, best semi-intervals and temporal intervals (full component and onset and offset phases) of the N400 component on Pearson r.

FIG. 4 depicts the outcome of the MAX strategy, with the comparisons among: 1) baselines (i.e., a single t-score at the peak); 2) best semi-intervals (SI); 3) component interval (Comp); 4) onset phase (ON); and 5) offset phase (OFF). The results are reported with and without the best cut-off (=40). In all the cases, the component interval and its onset phase provided the highest correlations. These correlations derived from neurophysiological/morphological features, match closely the results from the best of 10 semi-intervals obtained from the approach that only uses peak identification as the anchor from which to unfold the interval sets. Moreover, the component interval and the onset phase easily outperform the baseline (N400 peak latency).

The correlations obtained from the onset phase were higher than those in the offset phase. This result may be attributable to the synchronous firing of cells responsible for the onset of the observed N400 component.

Figure 5:
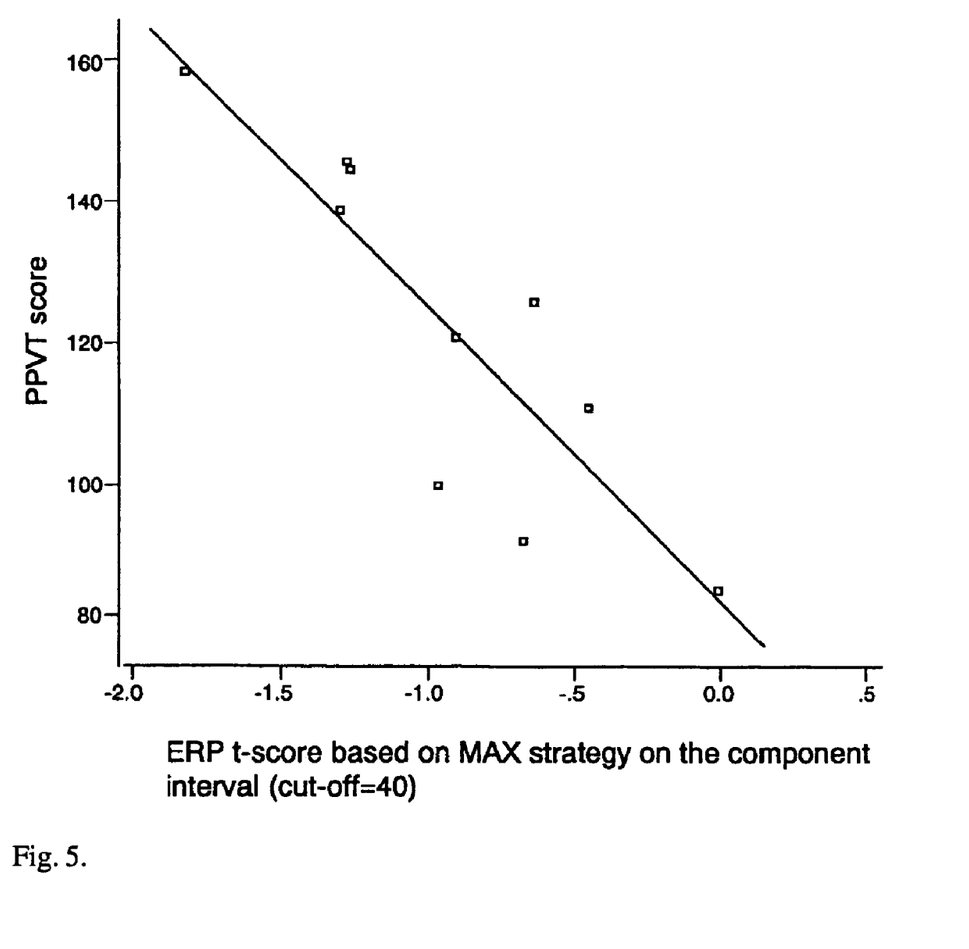
FIG. 5 is a graph showing scatter plot with the best correlations for linking neuropsychological and neurophysiological data (Pearson r=0.86). A linear relationship is shown between the component interval and the PPVT score.

Finally, the initial hypothesis states that a strong linear relation exists between features of the ERPs and PPVT-R scores. If such a relationship exists, it is possible to use ERPs for predicting future performance on the PPVT-R. FIG. 5 presents a scatter plot with the best statistical correlation (Pearson r=0.863). It confirms that the relationship is linear. When the best-fitting line (regression line) is calculated on this scatter plot, the following equation is obtained: [Predicted PPVT score=−42.46×S+82.57] with a standard error of the estimate equal to 13.4. In this equation, S represents the optimal strategy with the best cut-off, namely, S=M1 (CzPz) of the component The consequence of these results is that a method capable of measuring neuropsychological test performance in the total absence of behavior is now available. The strong relationship between ERP measures and test performance demonstrated in this study presents a compelling case for the proposition that ERPs obtained within the context of a neuropsychological test are capable of providing as accurate an assessment of performance as that obtained from the traditional administration of the test. This demonstration promises new levels of access to non communicative patient populations as well as new treatment opportunities for those for whom treatment has often been denied.

Normative and patient studies have demonstrated that ERPs can provide critical assessment information in situations in which traditional behavioral measures cannot be used (Connolly et al., 1999; Connolly and D'Arcy, 2000; Connolly et al., 2000). Currently, the evaluation of the cognitive abilities under investigation related to the presence or absence of a particular ERP component. The present study extends the capability of ERP assessment by developing a quantification procedure that links directly the neurophysiological and neuropsychological measures.

The findings demonstrate that known ERP responses are strongly and linearly correlated with performance on the PPVT-R, a test of both spoken word comprehension and vocabulary knowledge. The strength of the correlations is particularly impressive because the ERP recordings and the standard PPVT-R administration were not done simultaneously (this would have been impossible) but only within three days of each other. The key element of this relationship is a derived measure obtained from the mean of the t-scores between incongruent and congruent waveforms within the temporal interval that delimits the N400 component. Hence, using only ERP recordings it is possible to estimate closely an individual's performance on a traditional paper-and-pencil measure of receptive language ability.

The optimal result in the correlational analysis is obtained using the first level of the computerized PPVT in conjunction with a centro-parietal montage (Cz and Pz). Thus, the correlation is assessed using minimal information (i.e., one of three levels of difficulty and two electrodes positioned to record the N400). These minimal conditions allow for efficient set-up and testing (about 30 minutes overall), an especially critical issue in a clinical context in which fatigue can be a serious obstacle for assessing patient populations.

The current study examined a group of ten left-sided stroke patients, which is a sample size that is in the low range for a correlational analysis. In order to judge the impact of this kind of analysis technique that attempts to link neurophysiological and neuropsychological measures further work will have to replicate these results using a larger number of participants, other computerized tests and their associated ERP components. Alternative methods of assessing the relationship between ERP and neuropsychological test performance also may prove useful (Reinvang, 1999).

Tables

TABLE 1

Stroke-related injury locations (all in left hemisphere) for patient participants.

| Patient | Region |
|---------|--------|
| S01 | lacunar, internal capsule, caudate nucleus |
| S02 | frontal, subcortical (hemorrhage) |
| S03 | posterior frontotemporal, basal ganglia, (left carotid occlusion, middle cerebral artery distribution) |
| S04 | frontal-posterior, parietal (middle cerebral artery) |
| S05 | frontal |
| S06 | lacunar, pons |
| S07 | basal ganglia, deep hemisphere, anterior lateral ventricle, sub-cortical |
| S08 | no focal abnormality (left carotid occlusion, middle cerebral artery distribution) |
| S09 | frontal-posterior, insular cortex (middle cerebral artery), old right parietal-occipital infarct |
| S10 | parietal lobe (left carotid occlusion) |

The neuropsychological tests (and the relevant ERP components) that can be computer adapted and administered in such a manner as to permit the simultaneous recording of ERP are the following:

1. The Peabody Picture Vocabulary Test - Revised (PPVT-R) - PMN & N400
2. The Token Test - N2B, P300
3. The Backwards Digit Span of Wechsler Memory Scale - Third Edition (WMS-III) - P300
4. The Vocabulary Test of the Wechsler Adult Intelligence Scale - Revised (WAIS-R) - P300
5. The Vocabulary Test of the Wechsler Intelligence Scale for Children - Third Edition (WISC-III) - N200 & P300
6. Psycholinguistic Assessments of Language Processing in Aphasia. (PALPA) - P300

-continued

7. The Similarities Test of the Wechsler Adult Intelligence Scale - Revised (WAIS-R) - P300
8. The Similarities Test of the Wechsler Intelligence Scale for Children - Third Edition (WISC-III) - P300
9. Warrington Recognition Memory Test (WRMT) - Recognition Memory Word Test (RMW) - P300
10. Warrington Recognition Memory Test (WRMT) - Recognition Memory Face Test (RMF) - P300
11. Rosner Test - PMN & P300

What is claimed is:

1. A method for cognitive function assessment in a patient comprising:
   adapting a standardized psychometric test to a computer format to produce a computerized standardized psychometric neuropsychological test for presentation of stimuli to the patient;
   simultaneously presenting the test to the patient and recording the patient's event-related potential (ERP) obtained from an EEG (electroencephalogram) to generate ERP data;
   applying algorithms that relate the ERP data to behavioral data through a regression line in an interpretable manner within the context of standardized psychometric tests;
   using this regression line to interpret the ERP data within the context of standardized psychometric tests even in the absence of behavior/performance measures;
   and making prognosis of the patient using the ERP data;
   wherein the steps of the method are conducted in such a manner as to permit the evaluation of a patient's state of mental functioning using the ERP data even if the patient is unable to verbally or behaviorally perform the test in a typical fashion.

2. A method for cognitive function assessment in a patient comprising:
   adapting a neuropsychological test to a computer format to produce a computerized standardized psychometric neuropsychological test for presentation of stimuli to the patient;
   simultaneously presenting the test to the patient and recording the patient's electroencephalographic (EEG) signals to effect recording of late-occurring "cognitive" event-related potentials (ERP) from a number of locations on the patient's head to provide ERP data;
   applying a series of analysis algorithms that relate the ERP data to obtained behavioral data in an interpretable manner;
   applying a series of analysis algorithms that permit interpretation of the ERP data within the context of the test's framework even in the absence of behavioral data;
   and making a prognosis of patient outcome using the ERP data obtained using the test;
   wherein the steps of the method are conducted in such a manner as to permit the evaluation of a patient's state of mental functioning using the ERP data even if the patient is unable to verbally or behaviorally perform the test in a typical fashion.

3. The method according to claim 2 including using the steps of the method to evaluate patient progress through medical treatment using the ERP data obtained using the test.

4. The method according to claim 2 wherein the analysis algorithms use the Pearson correlation coefficient to evaluate the strength of an association between the ERP data and the obtained behavioral data.

5. The method according to claim 2 wherein the analysis algorithms use waveform features and parameters that maximize the correlation between the ERP data and test scores of the test.

6. The method according to claim 2 wherein the test applied assesses the function of semantic comprehension ability and wherein the analysis algorithms use the N400 component of the ERP data.

7. The method according to claim 2 wherein the test applied assesses the function of memory ability and wherein the analysis algorithms use the P300 and the LPC (late positive component) of the ERP data.

8. The method according to claim 2 wherein the analysis algorithms use a discrimination which is formally expressed using serial t-scores that provide a statistical method of comparing two waveforms on a point-by-points basis to establish where they differed in time.

9. The method according to claim 8 wherein the analysis algorithms used act to calculate the variance for each point in the waveform necessary to achieve the t-scores using homologous points in each of the trials that went into making up the two waveforms, wherein one waveform is congruent and the other is incongruent.

10. The method according to claim 8 wherein a succession of sums of t-scores is obtained for each of three levels of difficulty of the test across three electrode sites, the three sites being Fz, Cz and Pz.

11. The method according to claim 10 wherein the sums are calculated in a temporal interval that is both centered to the peak latency and increased in a step-wise fashion by 40 milliseconds, that is semi-intervals of 20 ms on each side of the peak.

12. The method according to claim 8 wherein the analysis algorithms obtain one baseline case that is composed of a single t-score at the peak and ten different sums of t-scores obtained from ten different semi-intervals varying by 20 ms from 20 ms to 200 ms.

13. The method according to claim 2 wherein the test comprises the first level of a computerized Peabody Picture Vocabulary Test PPVT in conjunction with a centro-parietal montage (Cz and Pz).

14. The method according to claim 2 wherein, if a linear relationship links certain elements of the ERP data to Peabody Picture Vocabulary Test-Revised PPVT-R scores, then the correlation coefficients that numerically express this relationship are used to elucidate which waveform features are critical.

15. The method according to claim 5 wherein the analysis algorithms are used to obtain the waveform features and strategies that provide the highest Pearson correlation between the ERP data and neuropsychological performance.

16. The method according to claim 8 wherein the analysis algorithms are used to obtain the sum of the t-scores between two compared waveforms for the patient at each or among any combination of electrodes for a temporal interval that is the sum that is correlated with the behavioral performance of the patient.

17. The method according to claim 8 wherein the analysis algorithms are used to take the highest sum of t-scores between two compared waveforms for the patient among any combination of electrodes for a temporal interval that is the highest value that is correlated with the behavioral performance of the patient.

18. The method according to claim 17 wherein the analysis algorithms are used to obtain the temporal interval and the combination of electrodes which produce the highest Pearson correlation between the ERP data and neuropsychological performance.

19. The method according to claim 18 wherein the equation for the linear regression is based on the highest Pearson correlation to predict behavioral performance using only ERP data measures which are comprised of features and strategies.

20. A method for cognitive function assessment in a patient comprising:
adapting a neuropsychological test to a computer format to produce a computerized standardized psychometric neuropsychological test for presentation of stimuli to the patient;
wherein the patient is unable to verbally or behaviorally perform the test in a typical fashion;
simultaneously presenting the test to the patient and recording the patient's electroencephalographic (EEG) signals to effect recording of late-occurring "cognitive" event-related potentials (ERP) from a number of locations on the patient's head to provide ERP data even in the absence of behavioral data from the test on the patient;
applying a series of analysis algorithms that relate the ERP data obtained in the test to obtained behavioral data in an interpretable manner;
applying a series of analysis algorithms that permit interpretation of the ERP data within the context of the test's framework;
and making a prognosis of patient outcome using the ERP data obtained using the test.

* * * * *